US011464756B1

(12) United States Patent
Darm

(10) Patent No.: US 11,464,756 B1
(45) Date of Patent: Oct. 11, 2022

(54) MECUNA PRURIENS, L-DOPA AND 5-HTP BASED DIETARY SUPPLEMENTS, PHARMACEUTICAL FORMULATIONS AND USES THEREOF

(71) Applicant: Jerry Darm, Lake Oswego, OR (US)

(72) Inventor: Jerry Darm, Lake Oswego, OR (US)

( * ) Notice: Subject to any disclaimer, the term of this patent is extended or adjusted under 35 U.S.C. 154(b) by 304 days.

(21) Appl. No.: 16/793,278

(22) Filed: Feb. 18, 2020

Related U.S. Application Data

(63) Continuation-in-part of application No. 15/984,200, filed on May 18, 2018, now abandoned.

(60) Provisional application No. 62/821,819, filed on Mar. 21, 2019, provisional application No. 62/596,310, filed on Dec. 8, 2017, provisional application No. 62/508,470, filed on May 19, 2017.

(51) Int. Cl.

| | |
|---|---|
| ***A61K 31/215*** | (2006.01) |
| ***A61K 31/405*** | (2006.01) |
| ***A61K 36/48*** | (2006.01) |
| ***A23L 33/15*** | (2016.01) |
| ***A23L 33/105*** | (2016.01) |
| ***A23L 33/175*** | (2016.01) |
| ***A61K 47/32*** | (2006.01) |

(52) U.S. Cl.
CPC .......... *A61K 31/215* (2013.01); *A23L 33/105* (2016.08); *A23L 33/15* (2016.08); *A23L 33/175* (2016.08); *A61K 31/405* (2013.01); *A61K 36/48* (2013.01); *A61K 47/32* (2013.01)

(58) Field of Classification Search
CPC .... A61N 2005/0644; A61N 2005/0651; A61N 2005/0652; A61N 2005/0663; A61N 5/0616
See application file for complete search history.

(56) References Cited

U.S. PATENT DOCUMENTS

| | | | |
|---|---|---|---|
| 4,778,794 | A | 10/1988 | Naruse et al. |
| 4,832,957 | A | 5/1989 | Dempski et al. |
| 4,920,122 | A | 4/1990 | Naruse et al. |
| 5,189,064 | A | 2/1993 | Blum et al. |
| 6,132,724 | A | 10/2000 | Blum |
| 6,207,699 | B1 | 3/2001 | Rothman |
| 6,384,088 | B1 | 5/2002 | Hinz |
| 6,403,657 | B1 | 6/2002 | Hinz |
| 6,548,551 | B2 | 4/2003 | Hinz |
| 6,660,777 | B2 | 12/2003 | Hinz |
| 6,743,770 | B2 | 6/2004 | Bell et al. |
| 6,759,437 | B2 | 7/2004 | Hinz |
| 6,955,873 | B1 | 10/2005 | Blum |
| 7,268,161 | B2 | 9/2007 | Hinz |
| 7,517,908 | B2 | 4/2009 | Krishnan et al. |
| 7,547,723 | B2 | 6/2009 | Hinz |
| 8,137,690 | B2 | 3/2012 | Hitzig |
| 8,741,319 | B2 | 6/2014 | Crain et al. |
| 9,399,039 | B1 | 7/2016 | Sabbagh et al. |
| 9,468,627 | B2 | 10/2016 | Jacobsen et al. |
| 2002/0040054 | A1 | 4/2002 | Hinz |
| 2002/0147153 | A1 | 10/2002 | Bell et al. |
| 2003/0181509 | A1 | 9/2003 | Hinz |
| 2004/0101575 | A1 | 5/2004 | Hinz |
| 2004/0121010 | A1 | 6/2004 | Hirsh et al. |
| 2004/0122104 | A1 | 6/2004 | Hirsh et al. |
| 2004/0132826 | A1 | 7/2004 | Hirsh et al. |
| 2004/0197377 | A1 | 10/2004 | Thompson |
| 2004/0229285 | A1 | 11/2004 | Hinz |
| 2006/0062859 | A1 | 3/2006 | Blum et al. |
| 2006/0079495 | A1 | 4/2006 | Blum |
| 2006/0094765 | A1 | 5/2006 | Coelingh Bennink et al. |
| 2006/0110325 | A1 | 5/2006 | Hinz |
| 2006/0135567 | A1 | 6/2006 | Hinz |
| 2006/0167032 | A1 | 7/2006 | Galer et al. |
| 2006/0178423 | A1 | 8/2006 | Hinz |
| 2007/0117844 | A1 | 5/2007 | Morillo et al. |
| 2007/0203080 | A1 | 8/2007 | Lipshutz |
| 2007/0213370 | A1 | 9/2007 | Morillo et al. |
| 2007/0292536 | A1 | 12/2007 | Kellermann |
| 2007/0293571 | A1 | 12/2007 | Hinz |
| 2009/0192166 | A1 | 7/2009 | Krishnan et al. |
| 2009/0234012 | A1 | 9/2009 | Hinz |
| 2009/0311795 | A1 | 12/2009 | Hinz |
| 2010/0104504 | A1 | 4/2010 | Moran |
| 2010/0189698 | A1 | 7/2010 | Willis |
| 2010/0286226 | A1 | 11/2010 | Morillo et al. |
| 2012/0149752 | A1 | 6/2012 | Hitzig |
| 2012/0258984 | A1 | 10/2012 | Morillo et al. |
| 2013/0338192 | A1 | 12/2013 | Krishnan et al. |
| 2014/0142140 | A1 | 5/2014 | Bird |
| 2014/0243363 | A1 | 8/2014 | Crain et al. |
| 2015/0132280 | A1 | 5/2015 | Lopez et al. |

(Continued)

FOREIGN PATENT DOCUMENTS

| | | | | |
|---|---|---|---|---|
| EP | 1637185 | A1 * | 3/2006 | ........... A61K 31/405 |
| JP | 2020-68734 | A | 5/2020 | |
| WO | 1998/048785 | A2 | 11/1998 | |
| WO | 2001/013904 | A2 | 3/2001 | |
| WO | 2001/026642 | A2 | 4/2001 | |
| WO | 2002/064090 | A2 | 8/2002 | |
| WO | 2003/061656 | A1 | 7/2003 | |
| WO | 2004/022043 | A1 | 3/2004 | |
| WO | 2004/037190 | A2 | 5/2004 | |
| WO | 2004/039361 | A1 | 5/2004 | |
| WO | 2004/089298 | A2 | 10/2004 | |
| WO | 2005/055920 | A2 | 6/2005 | |
| WO | 2005/112906 | A2 | 12/2005 | |
| WO | 2004/095631 | A2 | 8/2007 | |

(Continued)

*Primary Examiner* — Aaron J Kosar
(74) *Attorney, Agent, or Firm* — Wagenknecht IP Law Group PC

(57) ABSTRACT

A dietary supplement or pharmaceutical formulation of *Mecuna pruriens* and/or L-DOPA, and 5-hydroxy-tryptophan (5-HTP) in an extended release carrier; and administration of the dietary supplement or pharmaceutical formulation to reduce stress or anxiety, improve mood, improve sleep, improve focus or concentration, reduce alcohol or drug cravings, or reduce sugar cravings.

18 Claims, No Drawings

(56) References Cited

U.S. PATENT DOCUMENTS

2015/0147385 A1 5/2015 Helson

FOREIGN PATENT DOCUMENTS

| | | | |
|---|---|---|---|
| WO | 2007/111958 | A2 | 10/2007 |
| WO | 2008/140448 | A1 | 11/2008 |
| WO | 2009/003226 | A1 | 1/2009 |
| WO | 2009/042632 | A2 | 4/2009 |
| WO | 2009/091605 | A2 | 7/2009 |
| WO | 2011/087755 | A2 | 7/2011 |
| WO | 2011/119588 | A1 | 9/2011 |
| WO | 2012/054815 | A1 | 4/2012 |
| WO | 2013/007698 | A1 | 1/2013 |
| WO | 2014/180556 | A1 | 11/2014 |
| WO | 2015/073576 | A1 | 5/2015 |
| WO | 2015/077640 | A1 | 5/2015 |
| WO | 2016/001922 | A1 | 1/2016 |
| WO | 2016/001924 | A2 | 1/2016 |
| WO | 2016/106135 | A1 | 6/2016 |
| WO | 2016/179540 | A1 | 11/2016 |

* cited by examiner

MECUNA PRURIENS, L-DOPA AND 5-HTP BASED DIETARY SUPPLEMENTS, PHARMACEUTICAL FORMULATIONS AND USES THEREOF

CROSS REFERENCE TO RELATED APPLICATIONS

This is a continuation in part of U.S. patent application Ser. No. 15/984,200, filed May 18, 2018, which claims priority to U.S. provisional patent application No. 62/596,310, filed Dec. 8, 2017 and U.S. provisional patent application No. 62/508,470, filed May 19, 2017; each of which is herein incorporated by reference in its entirety.

This application also claims priority to U.S. provisional patent application No. 62/821,819, filed Mar. 21, 2019, which is herein incorporated by reference in its entirety.

TECHNICAL FIELD

The invention relates generally to formulations and methods for improving and protecting the general healthcare of subjects, and more specifically to formulations and dietary supplements including *Mecuna pruriens* and/or levodopa (L-DOPA), and 5-Hydroxy-tryptophan (5-HTP) in an extended release carrier.

BACKGROUND OF THE INVENTION

Dietary supplements are products intended to supplement a subject's diet. They include Vitamins, herbs, medicinal plants, extracts, amino acids and other substances that when ingested contribute to the general health of the subject. By improving general health, they also help prevent and accelerate healing from a number of diseases and everyday problems.

*Mecuna pruriens* or velvet bean, is a known supplemental source of Levodopa (L-DOPA). *Mecuna pruriens* is made of about 15% L-DOPA. L-DOPA is a precursor to catecholamines, such as dopamine and epinephrine (adrenaline). Increasing dopamine concentration in the brain is an approach used to treat a number of medical conditions and everyday problems. However, maintaining dopamine levels in the brain provides a technical challenge in that dopamine cannot cross the protective blood-brain barrier, but L-DOPA can. To this end, L-DOPA is often used in treatments where the object is to increase a local dopamine concentration in the brain, such as in the treatment of Parkinson's disease. However, L-DOPA is decarboxylated in the blood stream to dopamine, which reduces its availability to cross the blood-brain barrier over an extended period of time. To this end, L-DOPA is increasingly combined with carbidopa, such as for the treatment of Parkinson's. For example, SINEMET, offered by Merck, is a combination of L-DOPA and carbidopa and is used to treat Parkinson's and Parkinson's like symptoms (shakiness, stiffness, difficulty moving). Carbidopa, a decarboxylase inhibitor, prevents the breakdown of L-DOPA in the bloodstream so more L-DOPA can enter the brain. Carbidopa does not cross the blood brain barrier.

5-Hydroxy-tryptophan (5-HTP) is a chemical by-product of the protein building block L-tryptophan. 5-HTP acts in the brain and central nervous system by increasing the production of the chemical serotonin. Serotonin can affect sleep, appetite, temperature, sexual behavior, and pain sensation. Since 5-HTP increases the synthesis of serotonin, it is used for several diseases and conditions where serotonin is believed to play an important role including depression, insomnia, obesity, and others.

5-HTP is produced commercially by extraction from the seeds of an African plant known as *Griffonia simplicifolia*. 5-HTP can also be produced in the laboratory using genetically engineered microbial systems or yeast cells. For instance, U.S. Pat. No. 10,023,889 provides a modified bacterial phenylalanine 4-hydroxylase (P4H), which can be used to catalyze the tryptophan 5-hydroxylation reaction, thereby resulting in 5-HTP. Another approach for producing 5-HTP is described in U.S. Pat. No. 9,663,768, which provides a dual microbe system. Both U.S. Pat. Nos. 10,023,889 and 9,663,768 are herein incorporated by reference.

However, a challenge with administering 5-HTP is that it is decarboxylated in the bloodstream within about 45 minutes, which, like L-DOPA, reduces its availability to cross the blood-brain barrier over an extended period of time.

Accordingly, there remains a need to develop improved approaches for the extended release of both L-DOPA and 5-HTP within the bloodstream to permit continued passage of each across the blood-brain barrier.

SUMMARY OF THE INVENTION

The invention addresses the need to develop dietary supplements and pharmaceutical formulations that improve the continued availability of L-DOPA and 5-HTP in the bloodstream for passage across the blood-brain barrier for therapeutic and/or prophylactic treatment of medical conditions and to help relieve everyday problems. In particular, the invention provides dietary supplements and pharmaceutical formulations, which include *Mecuna pruriens* and/or L-DOPA, optionally with carbidopa, and 5-hydroxy-tryptophan (5-HTP) in an extended release carrier.

*Mecuna pruriens* can be provided in a range of concentrations, which may vary depending on the needs of the particular subject. As a nonlimiting example, *Mecuna pruriens* can be provided at a concentration from about 5 mg to about 750 mg. In further embodiments, *Mecuna pruriens* is provided at about 100 mg and in other embodiments, about 200 mg. L-DOPA when used in place of *Mecuna pruriens* can be provided at any suitable concentration, such as between about 5 mg to 750 mg, 100 mg, 200 mg, 500 mg or others. 5-HTP can also be provided in a range of concentrations, which may vary depending on the needs of the particular subject. As a nonlimiting example, 5-HTP is provided at a concentration from about 5 mg to about 250 mg, preferably about 75 mg in some instances and about 150 mg in others. The 5-HTP can be any suitable form, such as chemically synthesized or using recombinant DNA technology to produce expression systems that produce enzymes that generate 5-HTP.

In some embodiments, a ratio of *Mecuna pruriens* or L-DOPA to 5-HTP is about 4:3. As a nonlimiting example, *Mecuna pruriens* or L-DOPA can be provided at about 100 mg and 5-HTP at about 75 mg; or *Mecuna pruriens* or L-DOPA at about 200 mg, and 5-HTP at about 150 mg.

The dietary supplements and pharmaceutical formulations are provided in an extended release form to administer a dose of *Mecuna pruriens* or L-DOPA (and optionally carbidopa), and 5-HTP over a desired time frame. In some embodiments the extended release carrier releases *Mecuna pruriens* or L-DOPA, and 5-HTP for about 2-8 hours in vivo. In a further embodiment, *Mecuna pruriens* or L-DOPA, and 5-HTP are released for about 4 hours.

In some embodiments, the extended release carrier is a crosslinked polyacrylic acid polymer. Exemplary polyacrylic polymers are CARBOPOL polymers or a pharmaceutically acceptable derivative thereof. The CARBOPOL polymers can be a polymer of acrylic acid crosslinked with allyl sucrose or allyl pentaerythritol, a polymer of acrylic acid and C10-C30 akyl acrylate crosslinked with allyl pentaerythritol, or a polymer of polyethylene glycol and a long chain alkyl acid ester. Suitable CARBOPOL polymers may be any one or more of 71G NF, 971P NF, 974 P NF, 980 NF, 981 NF, 5984 EP, ETD 2020 NF, Ultrez 10 NF, 934 NF, 934P NF, 940 NF, 941 NF, or 1342 NF.

In embodiments where the extended release carrier is a water soluble methylcellulose and hydroxypropyl methylcellulose polymer, it is preferably METHOCEL or a pharmaceutically acceptable derivative thereof.

The dietary supplements and pharmaceutical formulations can also be supplemented with additional agents having beneficial effect. Among these include Vitamins, such as B6, Folic Acid, B12, and Vitamin C. In some embodiments the agent with beneficial effect is L-methylfolate. In some embodiments, the agent with beneficial effect is methylcobalamin. In some embodiments, the agent with beneficial effect is S-adenosylmethionine (SAM-E).

In some embodiments, the dietary supplements and pharmaceutical formulations include one or more additional agents such as dopamine, tyrosine, L-tyrosine, D,L-Phenylalanine, and/or N-acetyl-L-tyrosine, optionally in an extract. In some embodiments the dietary supplements and pharmaceutical formulations include a decarboxylase inhibitor, L-DOPA (in addition to *Mecuna pruriens*), or carbidopa.

In some embodiments the pharmaceutical formulation includes (or the dietary supplement is paired with) one or more drugs selected from a selective serotonin reuptake inhibitor (SSRI), a serotonin norepinephrine reuptake inhibitor, and an inhibitor of the catecholamine serotonin system. Exemplary, but non-limiting, serotonin reuptake inhibitors are fluoxetine (PROZAC, SARAFEM), citalopram (CELEXA, CIPRAMIL), fluvoxamine (FAVERIN, FEVARIN, FLOXYFRAL, DUMYROX, LUVOX), escitalopram (LEXAPRO, CIPRALEX), paroxetine (PAXIL, SEROXAT), and sertraline (ZOLOFT).

In some embodiments the pharmaceutical formulation includes (or the dietary supplement is paired with) one or more dopamine reuptake inhibitors. Exemplary dopamine reuptake inhibitors include, but are not limited to Amineptine (SURVECTOR), Altropane (O-587), Amfonelic acid (AFA), Benocyclidine (BTPC), DBL-58, Difluoropine (O-620), Fluorenol, GBR-12935, GYM-52895, Modafinil (PROVIGIL), RTI-229, RTI-55 (IOMETOPANE), Vanoxerine (GBR-12909).

In some embodiments, the dietary supplements and pharmaceutical formulations include a plant extract. Exemplary plant extracts include *ginseng*, green tea extract, *vicia laba, phanera, piliostigma, cassia, canavalin*, and *dalbergia*.

In some embodiments the dietary supplements and pharmaceutical formulations are provided in combination with a cannabinoid, such as one or more cannabinoid selected from the group consisting of tetrahydrocannabinol (THC), cannabidiol (CBD), cannabigerol (CBG) and cannabichromene (CBC).

In related aspects of the invention the dietary supplements and pharmaceutical formulations are provided to counter effects and conditions associated with insufficient serotonin levels and/or insufficient dopamine levels.

The dietary supplements and pharmaceutical formulations can be used to reduce stress or anxiety, improve sleep, improve mood, and improve focus or concentration. The dietary supplements and pharmaceutical formulations can also be used to reduce alcohol or drug cravings. The dietary supplements and pharmaceutical formulations can also be used to reduce sugar cravings. Such methods of treatment include providing a subject suffering from or at risk of suffering from one or more of the above conditions and administering to the subject an effective amount of the dietary supplement or pharmaceutical formulation.

In other embodiments, the pharmaceutical formulation is used to prevent or treat a medical condition associated with insufficient bioavailability of serotonin and/or insufficient bioavailability of dopamine. In particular, the pharmaceutical formulation can be used to prevent, treat or reduce unwanted symptoms associated with depression, obsessive compulsive disorder, panic attacks, schizophrenia, seasonal affective disorder, PMS, attention deficit disorder (ADD), attention deficit hyperactivity disorder (ADHD), learning disabilities, autism, Post-Traumatic Stress Disorder (PTSD), anxiety, chronic pain syndromes, fibromyalgia, irritable bowel syndrome, obesity, migraine headaches, and insomnia. Such methods include providing a subject suffering from or at risk of suffering from one or more of the medical conditions above and administering to the subject an effective amount of the pharmaceutical formulation.

The invention also provides a method of treating alcoholism or alcohol cravings in a subject, which includes: providing a subject suffering from alcoholism; and administering to the subject an effective amount of a pharmaceutical formulation disclosed herein.

The invention also provides a method of treating alcohol withdrawal in a subject, which includes: providing a subject suffer from or at risk of suffering from alcohol withdrawal; and administering to the subject an effective amount of a pharmaceutical formulation or dietary supplement disclosed herein.

The invention also provides a method of treating drug addiction or drug abuse in a subject, which includes: providing a subject suffering from drug addiction or drug abuse; and administering to the subject an effective amount of a pharmaceutical formulation disclosed herein. Among those that can be treated include opiate, methamphetamine, cocaine, and marijuana.

DETAILED DESCRIPTION OF PREFERRED EMBODIMENTS

The yin and yang of human behavior and indeed the entire animal kingdom is largely determined by the balance between two cascades of neurotransmitters in the brain which could generally be characterized as either stimulant or sedative. Pain and pleasure are modulated by these neurotransmitters and the organisms contact with the outer environment is interpreted through this brain chemistry. The simple approach, avoidance behaviors of lesser organisms becomes a symphony in the millions of synapses of the human brain. Through the use of rather large doses of amino acid neurotransmitter precursors in an attempt to achieve appetite suppression we and our colleagues have surprisingly observed dramatic changes in several chronic conditions which have previously been only partially treated or which have been unsuccessfully treated in the past.

The sedative cascade of neurotransmitters and their precursors begins with tryptophan which can travel through the blood brain barrier and produces 5-HTP which then becomes serotonin. Serotonin enhances our sense of well-being and seems to have a calming effect and is also associated with pain and pleasure. At night when the lights are out an enzyme in the pineal gland converts serotonin to Melatonin which then enhances sleep. Tryptophan was used extensively over the counter until several years ago when a bad batch which was contaminated with certain bacterial components caused death and disability in several users.

Recently 5-HTP has been introduced to the US market. 5-HTP is the direct precursor to serotonin and easily passes through the blood brain barrier while serotonin does not. Taking 5-HTP in any of several forms can raise serotonin levels in a natural way by "Filling the Well". There appears to be both a short term and long term results from taking 5-HTP. Short term there seems to be a 'burst' lasting 4-5 hours when levels rise, and long term as the "reservoir" or "water table" rises, to extend the metaphor, we notice that it takes much less 5-HTP to achieve the same result.

Our studies indicate effects of 5-HTP are definitely enhanced when combined with certain stimulating amino acid precursors. Tyrosine is a precursor to dopa which becomes dopamine which can be converted to norepinephrine and eventually epinephrine. By combining Tyrosine with 5-HTP or combining L-DOPA or *Mecuna pruriens* (optionally with carbidopa) with 5-HTP, the actions of 5-HTP are surprisingly and significantly enhanced and the list of disorders responding to amino acid therapy grows longer. In particular ADD and ADHD chronic fatigue syndrome and mild learning disabilities associated with inability to concentrate are helped. We have seen numerous adults and children and even one autistic child respond dramatically to these therapies which would traditionally be treated with amphetamines Rytalin or Adderol.

Without being bound by theory, we believe a neurotransmitter deficiency syndrome can manifest in a number of ways in each subject. Severe disorders ranging from autism and schizophrenia all the way to anxiety, panic, obsessive compulsive disorders, ADD and SAD can be lumped into the same category. Other disorders we have seen improve with the amino acid therapy include migraines, PMS, fibromyalgia, chronic fatigue syndrome, obsessive compulsive disorder and chronic pain. We have also noted reduced cravings in patients with certain forms of substance abuse including sedatives such as alcohol and stimulants such as cocaine. Chronic pain syndromes also respond. Behavioral disorders such as obsessive gambling, shopaholism and even aggressive criminal tendencies could theoretically improve. Sleep disorders could be treated non-narcotically. Finally, post-traumatic syndromes such as Gulf War syndrome and Vietnam PTSS could conceivably be treated.

We have also found that the compositions are effective at treating chronic conditions and the alleviation of unwanted symptoms by improved delivery of amino acid neurotransmitter precursors to persons who in the past have had little or no success with commonly prescribed medications. Further, these precursors together with beneficial agents increase the effectiveness of treatment and symptom relief by way of a beneficial nutritional cocktail.

The invention provides dietary supplements and pharmaceutical formulations, which include *Mecuna pruriens* and/or levodopa (L-DOPA), and optionally carbidopa, and 5-hydroxy-tryptophan (5-HTP), whether from extract or synthetically produced, in an extended release carrier, with preferably additional beneficial agents.

I. Compositions and their Use as Dietary Supplements and Pharmaceutical Formulations The dietary supplements of the invention can be used to counter effects associated with insufficient bioavailability of serotonin and/or insufficient bioavailability of dopamine and in particular can be used to prevent or reduce symptoms in a subject suffering from or at risk of suffering from conditions, such as stress, anxiety, insufficient sleep (e.g. insomnia), and poor mood (e.g. pessimistic worry, agitation, self-deprecation), decreased energy and libido, and abnormal hormonal circadian rhythms. In addition, the dietary supplements can improve focus and concentration in subjects. Still further, the dietary supplements can reduce alcohol, drug, and sugar cravings.

Relatedly, the pharmaceutical formulations can be used to prevent or treat a medical condition or disease associated with insufficient bioavailability of serotonin and/or insufficient bioavailability of dopamine. In particular, the pharmaceutical formulation can be used to prevent or treat depression, obsessive compulsive disorder, panic attacks, schizophrenia, seasonal affective disorder, PMS, attention deficit disorder (ADD), attention deficit hyperactivity disorder (ADHD), learning disabilities, autism, Post-Traumatic Stress Disorder (PTSD), anxiety, chronic pain syndromes, fibromyalgia, irritable bowel syndrome, obesity, migraine headaches, and insomnia. The pharmaceutical formulations also have particular utility in the treatment of alcoholism and drug addiction. The pharmaceutical formulation may be used to treat alcohol withdrawal.

The dietary supplements and pharmaceutical formulations are used to improve the general health and to treat a variety of symptoms and disorders. By "treat" it is meant that the dietary supplements and pharmaceutical formulations alleviate, abate or ameliorate a disease, disorder or condition symptoms; prevent additional symptoms; ameliorate or prevent the underlying metabolic causes of symptoms; inhibit the disease, disorder, or condition, e.g., arresting the development of the disease, disorder or condition; relieving the disease, disorder or condition, causing regression of the disease, disorder or condition; relieving a condition caused by the disease, disorder or condition; or stopping the symptoms of the disease, disorder or condition. The terms "treat," "treating" or "treatment", include, but are not limited to, prophylactic and/or therapeutic treatments.

The term "amelioration" of the symptoms of a particular disease, disorder or condition by administration of *Mecuna pruriens* and/or L-DOPA and 5-HTP refers to any lessening of severity, delay in onset, slowing of progression, or shortening of duration, whether permanent or temporary, lasting or transient that can be attributed to or associated with administration of the *Mecuna pruriens*, L-DOPA, and 5-HTP.

The primary active agents, *Mecuna pruriens*, L-DOPA (optionally carbidopa), and 5-hydroxy-tryptophan (5-HTP) are provided in an extended release carrier and presented in a dietary supplement and/or in a pharmaceutical formulation. The term "dietary supplement" refers to a dietary ingredient such as a Vitamin; mineral; herb or other botanical; amino acid; dietary substance for use by man to supplement the diet by increasing the total dietary intake; or a concentrate, metabolite, constituent, extract, or combination of the preceding substances. Dietary supplements are conventionally provided in forms such as tablets, capsules, softgels, gelcaps, powders, patches, and liquids. Whereas, the term "pharmaceutical" refers to a medicinal drug. The term "formulation" refers to a product that results from mixing or combining more than one active agent (e.g. *Mecuna pruriens* and/or L-DOPA and/or carbidopa and 5-HTP) and includes both fixed and non-fixed combinations of the active agents. The term "fixed combination" means that one active agent (e.g. *Mecuna pruriens*, L-DOPA, carbidopa) and a co-agent (5-HTP) are both administered to a subject simultaneously in the form of a single entity or dosage. The term "non-fixed combination" means that one active agent (e.g. *Mucuna pruriens*, L-DOPA, or carbidopa) and a co-agent (5-HTP) are administered to a subject as separate entities either simultaneously, concurrently or sequentially with no specific intervening time limits. In non-fixed combinations, *Mecuna pruriens* or L-DOPA or carbidopa and 5-HTP would each be in an extended release carrier. The latter also applies to cocktail therapy, e.g. the administration of three or more active agents.

A distinction between *Mecuna pruriens* and/or L-DOPA and/or carbidopa and 5-HTP for use as a dietary supplement versus as a pharmaceutical formulation depends on whether the combination is used to treat, diagnose, prevent, or cure diseases consistent with pharmaceutical use or whether the combination is used as a nutritional supplement consistent with use as a dietary supplement. As general guidance, administration of about 100 mg *Mecuna pruriens* or L-DOPA or carbidopa and about 75 mg 5-HTP would act as a nutritional supplement; whereas a pharmaceutical formulation would typically include a substantially higher dose to achieve a pharmaceutical effect.

The dietary supplements and pharmaceutical formulations include both *Mecuna pruriens* or L-DOPA or carbidopa, and 5-HTP in an effective amount. The term "effective amount" refers to a sufficient amount of *Mecuna pruriens* or L-DOPA or carbidopa and 5-HTP which will relieve or prevent to some extent one or more deleterious symptoms of the condition or disorder being treated, or will increase to some extent nutrition, general health or one or more desired effects. Nonlimiting examples of deleterious effects that can be relieved by the dietary supplements and pharmaceutical formulations include anxiety, sleep loss, poor mood (e.g. pessimistic worry, agitation, self-deprecation), alcohol cravings, drug cravings, and sugar cravings. Nonlimiting examples of desired effects that can be increased using the dietary supplements and pharmaceutical formulations include improved general health, calmness, increased focus or concentration, improved mood, and improved quality or amount of sleep. The pharmaceutical formulations can also be used to treat alcoholism and drug addiction, in particular, methamphetamine, opiate (e.g. heroin, morphine, oxycodone, hydrocodone, codeine, and fentanyl), cocaine, and marijuana addiction. The pharmaceutical formulations can also be used to treat depression, obsessive compulsive disorder, panic attacks, schizophrenia, seasonal affective disorder, PMS, attention deficit disorder (ADD), attention deficit hyperactivity disorder (ADHD), learning disabilities, autism, Post-Traumatic Stress Disorder (PTSD), anxiety, chronic pain syndromes, fibromyalgia, irritable bowel syndrome, obesity, migraine headaches, and Insomnia.

The dietary supplements and/or pharmaceutical formulations can be used to treat or ameliorate symptoms associated with serotonin deficiency disorders and dopamine deficiency disorders.

It is understood that an "effective amount" can vary from subject to subject due to variation in metabolism of *Mecuna pruriens*, L-DOPA, carbidopa and 5-HTP, genetics, age, weight, general condition of the subject, the condition being treated, and the severity of the condition being treated. By way of example only, the effective amount may be determined by experimentation. In particular, a dose can be increased or decreased depending on the results of a prior dose.

*Mecuna pruriens* can be provided at any suitable dose, but is typically provided from about 5 mg to about 750 mg. In some embodiments *Mecuna pruriens* is provided at about 100 mg. In others about 200 mg. L-DOPA when used in place of *Mecuna pruriens* can be provided at any suitable dose, such as between about 5 mg to 2,000 mg, 10 mg, 100 mg, 200 mg, 500 mg, 750 mg, 1,000 mg, or 1,500 mg. Likewise, carbidopa can be provided at any suitable dose, such as between about 5 mg to 2,000 mg, 10 mg, 100 mg, 200 mg, 500 mg, 750 mg, 1,000 mg, or 1,500 mg. 5-HTP is typically provided at a dose from about 5 mg to about 250 mg. In some embodiments, 5-HTP is provided at about 75 mg. In others, 150 mg. The formulation also typically provides more *Mecuna pruriens* than 5-HTP. In some embodiments the ratio of *Mecuna pruriens* or L-DOPA or carbidopa to 5-HTP is about 4:3. For example, if *Mecuna pruriens* or L-DOPA or carbidopa is provided at about 100 mg, 5-HTP can be provided at about 75 mg. Likewise, if *Mecuna pruriens* or L-DOPA or carbidopa is provided at about 200 mg, 5-HTP can be provided at about 150 mg.

*Mecuna pruriens*, L-DOPA, carbidopa and 5-HTP are preferably provided in an extended release carrier. The extended release carrier is a non-toxic compound that facilitates the delivery of *Mecuna pruriens*, L-DOPA, carbidopa and 5-HTP over a desired period of time. Providing *Mecuna pruriens*, L-DOPA, and 5-HTP in an extended release carrier provides an improvement in maintaining a consistent and regular dose of L-DOPA and 5-HTP across the blood-brain barrier and therefore helps maintain a steady local concentration of dopamine and serotonin. Further, by providing the biologically active agents in an extended release carrier, potential adverse effects associated with higher doses of these ingredients can be reduced or prevented. As a non-limiting example, it has been found that nausea and diarrhea can occur when taking 5-HTP. In the present invention, the extended release carrier reduces the amount of bioavailable 5-HTP compared to conventional formulations, which reduces nausea and diarrhea. Preferably, the extended release carrier releases *Mecuna pruriens*, L-DOPA, and/or carbidopa and 5-HTP for about 2-8 hours in vivo. More preferably the extended release carrier releases *Mecuna pruriens*, L-DOPA, and/or carbidopa and 5-HTP for about 4 hours in vivo.

Preferred extended release carriers include crosslinked polyacrylic acid polymers or water soluble methylcellulose and hydroxypropyl methylcellulose polymers. Polyacrylic polymers are typically characterized by repeating acrylic acid units. Accordingly, the molecular weight of such polymers vary widely. A variety of suitable polyacrylic acid polymers suitable for administration are known in the art. Among these include acrylic acid crosslinked with allyl sucrose or allyl pentaerythritol. Another is a polymer of acrylic acid and C10-C30 akyl acrylate crosslinked with allyl pentaerythritol. Still another is a polymer of polyethylene glycol and a long chain alkyl acid ester. The most preferred polymers are offered under the tradename CARBOPOL, which include 71G NF, 971P NF, 974 P NF, 980 NF, 981 NF, 5984 EP, ETD 2020 NF, Ultrez 10 NF, 934 NF, 934P NF, 940 NF, 941 NF, 1342 NF. In instances where the carrier is a water soluble methylcellulose and hydroxypropyl methylcellulose polymer, preferably the polymer is METHOCEL. Combining the compositions with an extended release carrier is typically performed according to methods disclosed in regards to the specific carrier, which can be obtained from the corresponding manufacturer or supplier.

The dietary supplements and pharmaceutical formulations can be formulated for administration by any suitable route such as oral, mucosal (e.g., nasal, sublingual, vaginal, buccal, or rectal), topical (dermal or transdermal) or parenteral (e.g., subcutaneous, intravenous, bolus injection, intramuscular, or intraarterial). As such, the dietary supplements and pharmaceutical formulations may be administered in a variety of dosage forms, such caplets, capsules, soft elastic gelatin capsules, cachets, troches, lozenges, dispersions, suppositories, ointments, cataplasms (poultices), pastes, powders, dressings, creams, plasters, solutions, patches, sustained release patches, aerosols (e.g., nasal sprays or inhalers), gels, liquid dosage forms suitable for oral or mucosal administration to a patient, including suspensions (e.g., aqueous or non-aqueous liquid suspensions, oil-in-water emulsions, or a water-in-oil liquid emulsions), elixirs; liquid dosage forms suitable for parenteral administration to a patient, and sterile solids (e.g., crystalline or amorphous solids) that can be reconstituted to provide liquid dosage forms suitable for parenteral administration to a patient, among others.

Preferably, the dietary supplements and pharmaceutical formulations are formulated for administration orally. Dietary supplements and pharmaceutical formulations for oral use include tablets which contain *Mecuna pruriens* and/or L-DOPA and/or carbidopa, 5-HTP and the extended release carrier in an admixture with non-toxic acceptable excipients. These excipients may be, for example, inert diluents, such as calcium carbonate, sodium chloride, lactose, calcium phosphate or sodium phosphate; granulating and disintegrating agents, for example, potato starch or alginic acid; binding agents, for example, starch, gelatin or acacia; and lubricating agents, for example, stearates or talc. Other acceptable excipients can be colorants, flavoring agents, plasticizers, humectants etc. The tablets may be uncoated or they may be coated by known techniques, optionally to delay disintegration and absorption in the gastrointestinal tract and thereby provide a sustained action over a longer period. For example, a time delay material such as glyceryl monostearate or glyceryl distearate may be employed in addition to the extended release carrier. Still further formulations for oral use may also be presented as chewing tablets, or as hard gelatin capsules where *Mecuna pruriens* and/or L-DOPA, and 5-HTP are mixed with an inert solid diluent, for example, calcium carbonate, calcium phosphate or kaolin, or as soft gelatin capsules wherein *Mecuna pruriens* and/or L-DOPA, and 5-HTP are mixed with water or an oil medium, for example, peanut oil, liquid paraffin, or olive oil.

While *Mecuna pruriens* provides a source of L-DOPA, it also provides additional beneficial effects that enhance the benefits of L-DOPA. Similarly, the dietary supplements and pharmaceutical formulations may also include additional beneficial agents that enhance the effect of *Mecuna pruriens*, L-DOPA, carbidopa or 5-HTP. The terms "enhance" or "enhancing" means to increase or prolong either in potency, duration or efficacy a desired effect. By way of example, "enhancing" the effect of *Mecuna pruriens*, L-DOPA, carbidopa and 5-HTP singly or in combination refers to the ability to increase or prolong, either in potency, duration and/or magnitude, the effect of the agents on the treatment of a disease, disorder or condition. Thus the term "enhance" is also intended to cover supplementing the effect of *Mecuna pruriens*, L-DOPA, carbidopa or 5-HTP by reducing additional undesired symptoms that are not affected or not substantially affected by *Mecuna pruriens*, L-DOPA, carbidopa or 5-HTP. When used in a subject, amounts effective for this use may depend on the severity and course of the disease, disorder or condition, previous therapy, the subject's health status and response to *Mecuna pruriens* or L-DOPA, and 5-HTP.

Among the agents that may enhance the effect of *Mecuna pruriens*, L-DOPA, carbidopa and 5-HTP include Vitamins, such as one or more of B6, Folic Acid, B12, and Vitamin C, and/or S-adensylmethionine (SAM-E). In particular, Vitamins B12, B6 and Folate may be added to improve the conversion of 5-HTP to serotonin and L-DOPA to dopamine. In addition to improving the conversion of precursors to both serotonin and dopamine, the additional agents can also provide other beneficial effects.

Vitamin B6, also called pyridoxine, is an essential nutrient and helps the body convert food (carbohydrates) into fuel (glucose). It is also believed to affect neurotransmitter synthesis. Inclusion of Vitamin B6 and/or its analogs in the dietary supplements and/or pharmaceutical formulations may improve mood, focus and/or concentration.

Folic Acid is another B Vitamin and is essential for proper synthesis of DNA, RNA and protein production. Recent research has indicated that folic acid supplements substantially reduce the incidence of Alzheimer's disease and stroke in healthy aging subjects. Sufficient amounts of folate are not readily available from food, and very small quantities of ingested folate ever reach the brain. Synthetic folic acid is more orally bioavailable than natural folate, but even synthetic folate presents challenges of efficient transportation across the blood-brain barrier. Intranasal delivery may improve drug bioavailability by direct absorption into the central nervous system, thereby avoiding extensive first-pass metabolism which may significantly lower the plasma concentrations of folic acid when it is administered via another route. To this end, L-methylfolate may be preferred over folic acid.

L-methylfolate is used by the body in the nutritional management of neurotransmitters (necessary chemicals) that affect mood. The importance of L-methylfolate in depression is that it, unlike folic acid, can cross the blood brain barrier to augment the activity of anti-depressants by acting as a trimonoamine modulator. A reduction in methylenetetrahydrofolate (MTHFR) activity leads to a decrease in the monoamine neurotransmitter pool, thereby rendering anti-depressant agents ineffective. Therefore, a nutritional supplement with combination of *Mecuna pruriens*, or L-DOPA, 5-HTP and L-methylfolate can be a good mood enhancer.

L-methylfolate dosage in the nutritional supplement formula is typically about 1 mg to 30 mg but could be higher. A dosage of about 7.5 mg or 15 mg taken orally once daily should improve depressive disorders. This same dosage can also be used for the distinct nutritional requirements of individuals who have suboptimal L-methylfolate levels in the cerebrospinal fluid, plasma, and/or red blood cells and have schizophrenia who present with negative symptoms and/or cognitive impairment, with particular emphasis as an adjunctive support for individuals who have stabilized on antipsychotics. These dosages formulated with the other amino acids may require adjustments based on renal dose adjustments, liver dose adjustments, and dialysis.

Vitamin B12 in the narrower sense frequently means cyanocobalamin, but there are also other compounds which are likewise covered by the generic term Vitamin B12; these are also referred to as cobalamins. It is intended herein that the term Vitamin B12 generally means all compounds which act as coenzyme in the human and/or animal body or can be converted into the corresponding coenzyme forms. These Vitamin B12 compounds have in common the Corrin structure with a trivalent cobalt as central atom and with a 5,5-dimethylbenzimidazole residue which is alpha-glycosidically linked via D-ribofuranose 3-phosphate. Most cobalamins differ from one another merely in one axial substituent. Examples of compounds which can be employed as Vitamin B12 are: cyanocobalamin (axial sub stituent=CN), aquocobalamin (B12a, axial substituent=—$O^+H_2$), hydroxocobalamin (B12b axial substituent=—OH), nitritocobalamin (B12c, axial sub stituent=—$NO_2$), 5'-deoxyadenosylcobalamin (coenzyme B12, axial sub stituent=5'-deoxyadenosyl) and methylcobalamin (methyl B12, axial sub stituent=—$CH_3$). Adenosylcobalamin and methylcobalamin are the active forms (coenzyme forms), and aquocobalamin and hydroxocobalamin are storage forms which likewise occur in the body.

Vitamin B12 has a key role in the functioning of the brain and also helps in the production of DNA, nerve and blood cells. Vitamin B12 may therefore also help to improve focus and concentration. Methylcobalamin is a coenzyme-type Vitamin B12 existing in blood and cerebrospinal fluid and is excellent in migrating ability to nervous tissues as compared with other B12 homologs. Biochemically, it exhibits a pharmacological action of accelerating metabolism of nucleic acids, proteins and lipids by methyl group rearrangement and thereby restoring damaged nervous tissues. Generally the effective dosage for Vitamin B12 is in a range of about 2.4 mcg or more and for children much lower amounts ranging from 0.4 mcg to 1.8 mcg. However, because the body does not efficiently absorb Vitamin B12, dosages provided in the dietary supplements and pharmaceutical formulations can vary. Further, people over age of 50 may require higher doses because they may not be producing enough of the protein called intrinsic factor (IF), which is essential for Vitamin B12 absorption. Without IF, only about 1% of the B12 from the supplement may being absorbed passively through the gut. Thus, dosage may depend on the bioavailability of IF, the regulation or supplementation of which may also be incorporated into nutritional supplement or pharmaceutical formulation.

Vitamin C helps repair and regenerate tissue, collagen, bone and provides numerous other benefits. It also fights stress and improves immunity to the external environment. Humans cannot synthesize their own Vitamin C. Vitamin C is typically provided from 75 mg to 1,000 mg but is more preferably about 250 mg to 500 mg.

S-Adenosyl Methionine (SAM-E) has been used to treat depression, migraines, bursitis, and is considered a supplement in the US. SAM-E is mostly consumed and produced in the liver, and acts as a regulator of processes including DNA methylation, amino acid metabolism, & immune reaction. SAM-e supports well-being and mood, promotes healthy brain function, supports joint & liver health, helps improve mental performance, and may help lessen symptoms of anxiety. For years people have taken SAM-E as a dietary supplement in efforts to improve their mood, and decrease symptoms of anxiety. SAM-E is sometimes taken for fatigue, difficulty concentrating, or for its anti-aging properties. As a supplement, SAM-E is typically provide at a dose from about 100 mg to about 500 mg.

The dietary supplements and pharmaceutical formulations can include or be paired with one or more agents such as dopamine, tyrosine, L-tyrosine, D,L-Phenylalanine, N-acetyl-L-tyrosine, a decarboxylase inhibitor, L-DOPA, and carbidopa.

Increased effectiveness of the *Mecuna pruriens*/5-HTP dietary supplement was found when including L-tyrosine at about 250 mg; however, dosages above and below 250 mg are also likely to be effective. A typical dose would be from 50 mg to 750 mg, but preferably from about 150 mg to 500 mg, with the majority of testing at 250 mg. L-Tyrosine is the precursor of the catecholamines; alterations in the availability of L-tyrosine to the brain can influence the synthesis of dopamine in experimental animals and probably in humans. In animals, stress increases the release of catecholamines, which can result in the depletion of their levels, an effect that can be corrected by giving L-tyrosine. L-Tyrosine does not seem to enhance the release of catecholamines when neurons are firing at their basal rates, but it does when firing rates are increased by stress.

Agents such as L-DOPA may supplement or enhance the effect of *Mecuna pruriens* since *Mecuna pruriens* itself is a source of L-DOPA. Carbidopa can also be used to enhance the effect of *Mecuna pruriens* and may permit administration of a lower dose. It has been found that when treating Parkinson's patients, co-administration of L-DOPA and carbidopa permits the dose of L-DOPA to be lowered by up to about 80%. Carbidopa works by preventing the breakdown of L-DOPA by decarboxylase enzymes. Since it cannot cross the blood brain barrier, carbidopa ensures the safe delivery of L-DOPA to the brain, where it becomes exposed to the action of the decarboxylases that generate dopamine. An example of L-DOPA/carbidopa combinations include those offered under the name SINEMET, such as SINEMET 25-100 (25 mg carbidopa/100 mg L-DOPA), SINEMET 10-100 (10 mg carbidopa/100 mg L-DOPA), and SINEMET 25-250 (25 mg carbidopa/250 mg L-DOPA). Preferably, L-DOPA and carbidopa are provided in a sustained release formula. As such, this effect is also expected when administering *Mecuna pruriens* with carbidopa.

Agents such as a decarboxylase inhibitor may reduce the conversion of 5-HTP to 5-HT and thus extend the presence of 5-HTP in the bloodstream, thereby extending its duration for crossing the blood-brain barrier. Carbidopa has decarboxylase activity and therefore prevents decarboxylation of both L-DOPA and 5-HTP. Therefore, carbidopa may be provided with 5-HTP and without or without *Mecuna pruriens* and L-DOPA.

The most commonly prescribed medications in the US are designed to raise serotonin in the brain inside the synapses between neurons. Unfortunately no new serotonin is created and eventually depletion or lowering of the "well" or "reservoir" can occur. At that point these medications are no longer as effective and going off them can create significant withdrawal symptoms which are frequently worse than the original symptoms. Indications for the serotonin re-uptake inhibitors such as Prozac, Effexor, Zoloft, Celexa, etc. include depression, anxiety, obsessive compulsive disorder, panic attacks, schizophrenia, seasonal affective disorder and PMS. We have seen all of these disorders and numerous other serotonin deficiency syndromes improve when we have treated them with the *Mucuna pruriens,* 5-HTP compositions and even more so with *Mecuna pruriens,* 5-HTP and L-tyrosine. When used in combination with serotonin re-uptake inhibitors they seem to enhance these drugs and we have not seen any signs or symptoms of serotonin overload.

The dietary supplements and pharmaceutical formulations can include or be paired with one or more agents such as a selective serotonin reuptake inhibitor (SSRI), a serotonin norepinephrine reuptake inhibitor, and an inhibitor of the catecholamine serotonin system. Such agents help maintain the local level of serotonin thereby permitting lower doses of 5-HTP or enhancing the effect of 5-HTP. Among the serotonin reuptake inhibitors that may be used in the pharmaceutical or paired with the dietary supplement include fluoxetine (PROZAC, SARAFEM), citalopram (CELEXA, CIPRAIVIIL), fluvoxamine (FAVERIN, FEVARIN, FLOXYFRAL, DUMYROX, LUVOX), escitalopram (LEXAPRO, CIPRALEX), paroxetine (PAXIL, SEROXAT), and sertraline (ZOLOFT).

The dietary supplements and pharmaceutical formulations can include or be paired with one or more dopamine reuptake inhibitors. Exemplary dopamine reuptake inhibitors include, but are not limited to, Amineptine (SURVECTOR), Altropane (O-587), Amfonelic acid (AFA), Benocyclidine (BTPC), DBL-58, Difluoropine (O-620), Fluorenol, GBR-12935, GYKI-52895, Modafinil (PROVIGIL), RTI-229, RTI-55 (IOMETOPANE), Vanoxerine (GBR-12909).

The dietary supplements and pharmaceutical formulations can include one or more beneficial plant extracts. Nonlimiting examples include *ginseng*, green tea extract, *vicia laba, phanera, piliostigma, cassia, canavalin*, and *dalbergia*. Each is added to further treat the subject consistent with its mode of action. *Ginseng* is believed to both boost the immune system and decrease the number and severity of colds in adults. Green tea extract is believed to increase alertness and thinking. Green tea extract is also taken to combat depression. *Vicia laba* or flax seed is a rich source of omega-3-fatty acids, and is high in antioxidants. *Phanera* is also high in antioxidants. The uses of *piliostigma, cassia, canavalin*, and *dalbergia* are less studied herein but may nonetheless be included.

In some embodiments, the dietary supplements and pharmaceutical formulations are provided in combination with a cannabinoid, such as one or more cannabinoid selected from tetrahydrocannabinol (THC), cannabidiol (CBD), cannabigerol (CBG) and cannabichromene (CBC). Cannabinoid receptors in the body regulate basic functions including mood, memory, appetite, pain, sleep, immune function, inflammation, neural development, neuroprotection, cardiovascular function, digestion and others. There are case reports demonstrating the benefit of cannabinoids in psychiatric symptoms and diseases, such as sleep disorders, anxiety disorders, bipolar disorders, and dysthymia. As such, inclusion of cannabinoids within the dietary supplements or pharmaceutical formulations can provide improvements in health and well-being.

Cannabinoid type I (CB1) receptors are mostly present in the brain and spinal cord. CB1 receptors in the hypothalamus, which is involved with appetite regulation, and the amygdala, play a role in memory and emotional processing. CB1 receptors are also found in nerve endings where they act to reduce sensations of pain. Cannabinoid type II (CB2) receptors tend to be found in the peripheral nervous system. They are especially concentrated in immune cells. When CB2 receptors are activated, they work to reduce inflammation. Inflammation is an immune response which is believed to play a role in many diseases and conditions. Like CB1 receptors, CB2 receptors are class A serpentine receptors that couple primarily to G-proteins to modulate an array of signaling pathways: adenylyl cyclase, mitogen-activated protein kinase (MAPK (p44/42 and p38)), c-Jun N-terminal kinase, Akt kinase/protein kinase B, phosphoinositide 3-kinase/Akt nuclear factor κ-light-chain-enhancer of activated B cells, nuclear factor of activated T cells, cAMP response element-binding protein/activating transcription factor, Janus kinase/signal transducer and activator of transcription, sphingomyelinase, and caspase, as well as some potassium and calcium ion channels. In some embodiments, agonists of CB2 receptors tend to be more favored by the compositions and methods as they do not appear to induce psychotropic effects found when activating CB1 receptors. However, negative allosteric modulators of CB1 receptors may also be preferred to prevent or reduce activation of CB1 receptors, such as in the treatment of drug abuse.

Cannabidiol (CBD) is the main nonpsychoactive component of *Cannabis sativa* plant. Human trials of CBD have demonstrated it is an effective antipsychotic, yet CBD is considered to be safe and well-tolerated, thereby decreasing risk associated with conventional antipsychotic drugs. While THC binds both CB1 and CB2 receptors, CBD is a negative allosteric modulator of the CB1 receptor—meaning it doesn't bind directly but rather interacts allosterically with the CB1 receptor to change its shape to weaken its ability to bind target.

Although CBD has little binding affinity for either of the two cannabinoid receptors (CB1 and CB2) CBD modulates several non-cannabinoid receptors and ion channels. The scientific literature has identified more than 65 molecular targets of CBD. For example, CBD also functions as a positive allosteric receptor modulator of the GABA-A receptor, which means that it interacts with the GABA-A receptor in a way that enhances the receptor's binding affinity for its principal endogenous agonist, gamma-Aminobutyric acid (GABA), which is the main inhibitory neurotransmitter in the mammalian central nervous system. The sedating effects of Valium and other Benzos are mediated by GABA receptor transmission. CBD reduces anxiety by changing the shape of the GABA-A receptor in a way that amplifies the natural calming effect of GABA.

At high concentrations, CBD affects the 5-HT1A (hydroxytryptamine) serotonin receptor, resulting in an antidepressant effect. CBD also binds to transient receptor potential cation channel subfamily V 1 (TRPV-1) receptors, which also function as ion channels. TRPV1 is known to mediate pain perception, inflammation and body temperature. Furthermore, some studies indicate that CBD may also function as an antagonist that blocks, or deactivates, another G protein-coupled receptor known as GPR55. GPR55 has been dubbed an "orphan receptor" because scientists are still not sure if it belongs to a large family of receptors. Some researches postulate that GPR55 may actually be a third cannabinoid receptor type. GPR55 is widely expressed in the brain, especially in the cerebellum, involved in modulating blood pressure and bone density. GPR55 promotes osteoclast cell function, which facilitates bone reabsorption.

Like other drugs that affect multiple brain receptors, high doses of CBD may not be as effective as lower doses. CBD may have an inverted-U effect over a dose range, which may be based on differences in sensitivity for the different targets. Lower doses of CBD impact fewer neural targets. Lower CBD doses in humans have been shown to be effective at reducing anxiety in individuals with generalized social anxiety disorder, and low to moderate doses are effective at reducing stress and improving performance in a simulated public speaking event. These positive effects are associated with a restoration of normal brain activity in key regions associated with anxiety and emotional dysregulation. As guidance and with respect to CBD oils, 2 mg would be a very low dose, 10-25 mg would be a low to moderate dose, and 50 mg and over would be a higher dose. Naturally, such dosages may vary by weight and thus are considered nonlimiting but rather a preliminary guide.

II. Monitoring and Adjusting Dosage of Pharmaceutical Formulations

The serotonin and the catecholamine (e.g., dopamine) neurotransmitter system work together as one system, and low levels of neurotransmitters in the system are believed to be associated with conditions to be treated or affected by the formulations disclosed herein. That is, dysfunction of the neurons of the central nervous system in general can give rise to the medical conditions and symptom to be treated.

Accordingly, by monitoring metabolized levels of neurotransmitters in a subject's body, a neurotransmitter profile can be established and monitored over time in response to administration of the formulations. Adjustments to dosage or frequently can then be made and the effects monitored.

As a nonlimiting example, a neurotransmitter profile can include a panel of one or more of serotonin, dopamine, acetylcholine, norepinephrine, epinephrine, glutamate, tryptophan, GABA and others. Neurotransmitter profiles can be established by testing for the presence, absence or amount of a corresponding analyte from one more biological samples, such as serum, saliva, urine, blood and others. Testing can be by way of a variety of analyte detection and quantifying methodologies. For example, detection and quantifying analytes from samples can be by way of enzyme-linked immunosorbent assay (ELISA). In general, neurotransmitter analysis is best done with samples collected 5 to 6 hours before bedtime. Though nonlimiting, it is believed that that testing should be done every 4 to 6 weeks to maintain the neurotransmitter profile.

Neurotransmitter profiling of blood or serum is likely to be the most sensitive and reflective of concentrations in circulation. However, blood or serum analysis tends to be a snapshot in time rather than an average over a prolonged period. Saliva can also be used but also tends to be variable due to the rapid responsiveness of the body. When using saliva, it is recommended to collect samples over a period of time, then assay and average the results to obtain an approximate value of neurotransmitters in the samples.

Neurotransmitter profiling of urine samples is a preferred approach since urine is collected in the bladder for few hours before the sample is drawn and therefore is a collective reflection of the neurotransmitter levels for least couple of hours. To reduce variability in urine sample analysis, measuring creatinine values and creating a ratio of neurotransmitter levels in micrograms to creatinine in grams can be performed. The dosage of the dietary supplement or the pharmaceutical formulation can be adjusted according to whether the subject is responding to it by monitoring the increasing, stabilizing, or decreasing neurotransmitter levels.

III. Significant Calming and Focus Identified in Subjects Having Stress-Related Disorders The invention provides a method of reducing symptoms association with Post-Traumatic Stress Disorder (PTSD) in a subject, which includes providing a subject suffering from PTSD; and administering to the subject an effective amount of a dietary supplement and/or pharmaceutical formulation disclosed herein.

Post-Traumatic Stress Disorder (PTSD) is a disorder that develops in some people who have experienced a shocking, scary, or dangerous event. However, not everyone with PTSD has been through a dangerous event. Some experiences, like the sudden, unexpected death of a loved one, can also cause PTSD. Symptoms usually begin early, within 3 months of the traumatic incident, but sometimes they begin years afterward. Symptoms must last more than a month and be severe enough to interfere with relationships or work to be considered PTSD. The course of the illness varies. Some people recover within 6 months, while others have symptoms that last much longer. In some people, the condition becomes chronic.

A study was conducted with cooperation of the VA, where several patients suffering from PTSD were given a combination of *Mecuna pruriens* (100 mg), 5-HTP (75 mg), L-Tyrosine (250 mg) daily, taken orally. Patients consistently showed significant calming and increased focus. Furthermore, the patients did not suffer from a drug hangover as with previously used medications.

Relatedly, and in accordance with the above, the invention also provides a method of reducing stress or anxiety in a subject, which includes providing a subject suffering from stress or anxiety; and administering to the subject an effective amount of a dietary supplement and/or pharmaceutical formulation disclosed herein.

Stress and anxiety can be symptoms of a serotonin deficiency. While there are many different types of stress and anxiety disorders, there are a few symptoms that most stress and anxiety disorders have in common. These include difficulty sleeping, muscle aches, fatigue, headaches, frequent nightmares, and panic attacks (rapid heart rate, sweating, shaking, shortness of breath, dizziness, nausea), pessimistic worry, agitation, self-deprecation. As such, the above symptoms may suggest the subject is suffering from stress or anxiety for purposes of the invention.

To study the effect of the composition on symptoms associated with stress, a subject known to regularly have panic attacks was able to abort her symptoms in 15-30 minutes after taking only one dose of a combination of *Mecuna pruriens* (100 mg), 5-HTP (75 mg), L-Tyrosine (250 mg) taken orally.

In addition, the invention also provides a method of treating a condition in a subject, which includes providing a subject suffering from the condition; and administering to the subject an effective amount of a dietary supplement or pharmaceutical formulation disclosed herein, wherein the condition is one or more selected from the group consisting of depression, panic attacks, seasonal affective disorder, PMS, anxiety, and insomnia or lack of sleep.

IV. Significant Focus and Improved Concentration Identified in Subjects Having Learning Disorders The invention also provides a method of improving focus or concentration in a subject, which includes providing a subject in need of improved focus or concentration; and administering to the subject an effective amount of a dietary supplement and/or pharmaceutical formulation disclosed herein.

A pilot study was conducted with children previously diagnosed with ADD and ADHD, which would traditionally have been be treated with amphetamines Rytalin or Adderol. The subjects were given a combination of *Mecuna pruriens* (100 mg), 5-HTP (75 mg), L-Tyrosine (250 mg) daily, taken orally. After continued treatment, improved focus and concentration was observed in the subjects.

In another study, an autistic 20 year old achieved 100% improvement from her symptoms after one month of therapy with a combination of *Mecuna pruriens* (100 mg), 5-HTP (75 mg), L-Tyrosine (250 mg) daily, taken orally.

In another study, a patient with schizophrenia who was in an outpatient program at the Meninger Clinic had dramatic improvement to the point of becoming employable and traveling about the country and by his own admission 82% better after several months of therapy. This outpatient was given a combination of *Mecuna pruriens* (100 mg), 5-HTP (75 mg), L-Tyrosine (250 mg) daily, taken orally.

Accordingly, the invention also provides a method of treating a condition in a subject, which includes providing a subject suffering from the condition; and administering to the subject an effective amount of a dietary supplement or pharmaceutical formulation disclosed herein, wherein the condition is one or more selected from the group consisting of obsessive compulsive disorder, schizophrenia, attention deficit disorder (ADD), attention deficit hyperactivity disorder (ADHD), learning disabilities, and autism.

V. Significantly Reduced Alcohol Cravings Identified in Subjects

The invention also provides a method of reducing alcohol and drug cravings in a subject, which includes providing a subject suffering from alcohol or drug cravings; and administering to the subject an effective amount of a dietary supplement and/or pharmaceutical formulation disclosed herein.

Even though many feel calmer after the first one or two drinks, the body is processing the alcohol and the physiological effects can actually trigger feelings of anxiety. Drinking alcohol can temporarily boost serotonin levels, therefore making you feel happier, but in the long term, excess alcohol can actually lower serotonin levels, and therefore either causing or exacerbating depression. Long-term alcohol use can have multiple negative effects on the body and aggravate existing anxiety.

Recent studies have shown that heavy drinking or long term drinking stresses the body and causes it to have higher levels of the stress hormone, cortisol. Cortisol is necessary in short term stress situations because it helps focus alertness and attention, but cortisol also suppresses bodily functions such as wound repair, bone growth, digestion, and reproduction. Chronically high cortisol levels therefore interfere with these important processes in the body. Furthermore, alcohol use also depletes the body of vitamin B6 and folic acid, which the body needs to help cope with stress. Long-term exposure to alcohol reduces the levels of the GABA-benzodiazepine receptor in the central nervous system and reduces the brain's ability to calm the mind and the body and cope with anxiety in the long run.

To study the effect of the compositions as a potential supplement to reduce alcohol cravings and as a potential treatment of alcoholism, a study was conducted where subjects identified as alcoholic were given a combination of *Mecuna pruriens* (100 mg), 5-HTP (75 mg), L-Tyrosine (250 mg) daily, taken orally. Results showed a significant loss in alcohol cravings. One subject was able to drink a glass of wine without the impulse to finish the bottle.

These reduced cravings suggest the invention can also provide a method of treating alcoholism in a subject or at least treatment of alcohol withdrawal, which includes providing a subject suffering from alcoholism; and administering to the subject an effective amount of a pharmaceutical formulation disclosed herein.

VI. Treatment of Drug Addiction

Positive results in the use of the compositions to reduce alcohol cravings were then tested as a potential treatment for those that abuse drugs. The invention also provides a method of reducing drug withdrawal symptoms and for treating drug addiction in a subject, which includes providing a subject suffering from drug addiction; and administering to the subject an effective amount of a pharmaceutical formulation disclosed herein. Examples include addiction to methamphetamine, opiate (e.g. heroin, morphine, oxycodone, hydrocodone, codeine, and fentanyl), cocaine, and marijuana.

Some of the most pronounced effects of drug use appear in the brain. All drugs interact with the brain in some way, and most affect how it communicates with other parts of the body. Specifically, many drugs interact with the brain's neurotransmitters, which serve as the messengers for the brain's communication system. Two neurotransmitters commonly affected by drug abuse are dopamine and serotonin. Drugs that manipulate dopamine affect a person's motivation, motor functioning, sense of pleasure and the salience of stimuli or events that he experiences. Drugs that affect serotonin, on the other hand, influence the ways that a person learns, remembers, sleeps, and feels emotions.

Alcohol and cocaine affect the brain in certain but distinct ways. Alcohol, for example, increases the levels of serotonin in very select parts of the brain. Cocaine, conversely, increases serotonin levels generally across many different areas of the brain, and does so by blocking reuptake of the neurotransmitter.

After abusing opiates for more than a few weeks, the brain in more than likely depleted of dopamine, serotonin, GABA, and acetylcholine. Opiates tend to produce 2 to 10 times the level of dopamine in the brain. In response, the brain responds to these surges by automatically producing less and less natural dopamine. So when you stop using drugs—your brain's naturally occurring "feel good" neurotransmitters, (namely serotonin and dopamine) are substantially below their normal levels. As a result, you may feel flat, lifeless, depressed, nervous, anxious, queasy—unable to enjoy the things that used to bring you pleasure.

It was hypothesized that the compositions of the invention could be used to treat those addicted to drugs or a least to lessen the negative effects associated with drug withdrawal during treatment, such as from cocaine, opiates, and methamphetamine, among others. Patients with a history of drug abuse including cocaine, opiates and methamphetamine were give a combination of *Mecuna pruriens* (100 mg), 5-HTP (75 mg), L-Tyrosine (250 mg) daily, taken orally. Patients reported significantly fewer drug cravings than prior to treatment.

In view of the studies above, and the known effects of various drugs on brain chemistry, the previous studies with compositions suggest use of the compositions for the treatment of drug cravings.

VII. Relief from Chronic Pain

Fibromyalgia syndrome affects the muscles and soft tissue. Symptoms include chronic muscle pain, fatigue, sleep problems, and painful tender points or trigger points. To study the effect of the compositions as a chronic pain reliever, subjects diagnosed with Fibromyalgia were given a combination of *Mecuna pruriens* (100 mg), 5-HTP (75 mg), L-Tyrosine (250 mg) daily, taken orally. Preliminary results show thirty to forty Fibromyalgia patients have experienced 50-90% relief of symptoms.

In another study, three chronic pain patients have achieved complete pain relief from their long standing chronic severe organically demonstrable pain syndromes after taking a combination of *Mecuna pruriens* (100 mg), 5-HTP (75 mg), L-Tyrosine (250 mg) daily, taken orally.

Accordingly, the invention also provides a method of reducing or treating chronic pain in a subject, which includes providing a subject suffering from chronic pain; and administering to the subject an effective amount of a dietary supplement or pharmaceutical formulation disclosed herein.

VIII. Reduction of SSRI when Combined with *Mecuna pruriens* and 5-HTP

The selective serotonin reuptake inhibitors (SSRIs) are the most commonly prescribed antidepressants. They can ease symptoms of moderate to severe depression. SSRIs ease depression by increasing levels of serotonin in the brain. SSRIs may also be used to treat anxiety disorders. SSRIs are called selective because they seem to primarily affect serotonin, not other neurotransmitters. All SSRIs work in a similar way and generally can cause similar side effects, though some people may not experience any. Possible side effects of SSRIs may include, among others drowsiness, nausea, dry mouth, insomnia, diarrhea, nervousness, agitation or restlessness, dizziness, sexual problems, such as reduced sexual desire or difficulty reaching orgasm or inability to maintain an erection (erectile dysfunction), headache, and blurred vision. Therefore, reducing the dose of SSRIs could decrease these potential side effects.

To study the effect of the compositions as a supplement to reduce the dosage of SSRIs, a subject previously taking fluoxetine (PROZAC), was given a combination of *Mecuna pruriens* (100 mg), 5-HTP (75 mg), L-Tyrosine (250 mg) daily, taken orally. The subject found that the fluoxetine (PROZAC) could be reduced by half while taking *Mecuna pruriens*/5-HTP/L-Tyrosine daily (orally).

Accordingly, it has been shown that administration of *Mecuna pruriens*/5-HTP/L-Tyrosine can reduce the dosage of SSRIs, such as fluoxetine. Since SSRIs work in a similar way, it also believed to be effective with citalopram fluvoxamine, escitalopram, paroxetine, and sertraline.

IX. Reduction of Sugar and Food Cravings

There are studies indicating brain chemical or neurotransmitter imbalances can cause sugar cravings as well as anxiety and depression. There is a strong connection between stress eating, comfort eating, emotional eating and low levels of the brain chemicals serotonin, GABA and endorphins.

The base compositions herein were initially designed for the treatment of obesity. Subjects identified as obese were provided a combination of *Mecuna pruriens* (100 mg), 5-HTP (75 mg), L-Tyrosine (250 mg) daily, taken orally. Subjects reported significantly decreased sugar cravings and overall weight loss. To this end, the invention also provides a method of reducing sugar cravings and for weight loss in a subject, which includes providing a subject suffering from sugar cravings and/or obesity; and administering to the subject an effective amount of a dietary supplement and/or pharmaceutical formulation disclosed herein.

EXAMPLES

Example I

Exemplary Dietary Supplement

A preferred dietary supplement for oral administration is set forth in TABLE 1.

TABLE 1

| Agent | Amount |
|---|---|
| Mecuna pruriens or L-DOPA | 100 mg |
| 5-HTP | 75 mg |
| Carbopol | 52 mg |
| Vitamin B6 | 10 mg |
| Folic Acid | 100 mcg |
| L-Tyrosine | 200 mg |
| B12 | 100 mcg |

Example II

Exemplary Dietary Supplement

An exemplary dietary supplement for oral administration is set forth in TABLE 2.

TABLE 2

| Agent | Amount |
|---|---|
| Mecuna pruriens or L-DOPA | 100 mg |
| 5-HTP | 75 mg |
| Carbopol | 52 mg |
| Vitamin B6 | 10 mg |
| L-methylfolate | 10 mg |
| L-Tyrosine | 200 mg |
| Methylcabalamin | 100 mcg |
| CBD | 10 mg |

Example III

Exemplary Pharmaceutical Formulation

A preferred pharmaceutical formulation for oral administration is set forth in TABLE 3.

TABLE 3

| Agent | Amount |
|---|---|
| Mecuna pruriens or L-DOPA | 200 mg |
| 5-HTP | 150 mg |
| Fluoxetine | 5 mg |
| Carbopol | 104 mg |
| Vitamin B6 | 20 mg |
| Folic Acid | 200 mcg |
| L-Tyrosine | 400 mg |
| B12 | 200 mcg |

Example IV

Exemplary Pharmaceutical Formulation

An exemplary pharmaceutical formulation for oral administration set forth in TABLE 4.

TABLE 4

| Agent | Amount |
|---|---|
| Mecuna pruriens or L-DOPA | 200 mg |
| 5-HTP | 150 mg |
| Fluoxetine | 5 mg |
| Carbopol | 104 mg |
| Vitamin B6 | 20 mg |
| L-methylfolate | 20 mg |
| L-Tyrosine | 400 mg |
| B12 | 200 mcg |
| CBD | 60 mg |

What is claimed is:

1. A dietary supplement or pharmaceutical formulation comprising 5-hydroxy-tryptophan (5-HTP) in an extended release carrier, wherein the dietary or pharmaceutical formulation is provided with one or more additional agents selected from the group consisting of S-adenosylmethionine (SAM-E), dopamine, tyrosine, D,L-Phenylalanine, and N-acetyl-L-tyrosine, optionally in an extract.

2. The dietary supplement or pharmaceutical formulation according to claim 1, further comprising *Mecuna pruriens* or L-DOPA, optionally at a concentration from about 5 mg to about 750 mg, preferably about 100 mg.

3. The dietary supplement or pharmaceutical formulation according to claim 2, wherein:

a ratio of *Mecuna pruriens* or L-DOPA to 5-HTP is about 4:3,

*Mecuna pruriens* or L-DOPA is provided at about 100 mg and 5-HTP is provided at about 75 mg, or 5-HTP is provided in a concentration from about 5 mg to about 250 mg, optionally about 75 mg.

4. The dietary supplement or pharmaceutical formulation according to claim 1, wherein the extended release carrier releases 5-hydroxy-tryptophan (5-HTP) for about 2-8 hours in vivo, or about 4 hours.

5. The dietary supplement or pharmaceutical formulation according to claim 1, wherein the extended release carrier is a crosslinked polyacrylic acid polymer or is a water soluble methylcellulose and hydroxypropyl methylcellulose polymer.

6. The dietary supplement or pharmaceutical formulation according to claim 1, further comprising one or more Vitamins, optionally selected from the group consisting of B6, Folic Acid, L-methylfolate, B12, methylcobalamin, and Vitamin C.

7. The dietary supplement or pharmaceutical formulation according to claim 1, provided with a decarboxylase inhibitor, L-DOPA, or carbidopa.

8. The dietary supplement or pharmaceutical formulation according to claim 1, provided with a compound selected from the group consisting of a selective serotonin reuptake inhibitor (S SRI), a serotonin norepinephrine reuptake inhibitor, an inhibitor of the catecholamine serotonin system, and a combination thereof, wherein:

the serotonin reuptake inhibitor is optionally selected from the group consisting of fluoxetine, citalopram, fluvoxamine, escitalopram, paroxetine, and sertraline.

9. The dietary supplement or pharmaceutical formulation according to claim 1, further comprising a plant extract, optionally selected from one or more of the group consisting of *ginseng*, green tea extract, *vicia laba, phanera, piliostigma, cassia, canavalin*, and *dalbergia*.

10. The dietary supplement or pharmaceutical formulation according to claim 1, further comprising a cannabinoid, optionally selected from one or more of the group consisting of tetrahydrocannabinol (THC), cannabidiol (CBD), cannabigerol (CBG) and cannabichromene (CBC).

11. A method of reducing stress or anxiety in a subject, comprising:

a) providing a subject suffering from stress or anxiety;
b) administering to the subject an effective amount of the dietary supplement or pharmaceutical formulation according to claim 1; and optionally,
c) monitoring a neurotransmitter profile of the subject over time.

12. A method of improving sleep in a subject, comprising:

a) providing a subject suffering from lack of sleep;
b) administering to the subject an effective amount of the dietary supplement or pharmaceutical formulation according to claim 1; and optionally,
c) monitoring a neurotransmitter profile of the subject over time.

13. A method of improving mood in a subject, comprising:

a) providing a subject in need of improved mood;
b) administering to the subject an effective amount of the dietary supplement or pharmaceutical formulation according to claim 1; and optionally,
c) monitoring a neurotransmitter profile of the subject over time.

14. A method of improving focus or concentration in a subject, comprising:

a) providing a subject in need of improved focus or concentration;
b) administering to the subject an effective amount of the dietary supplement or pharmaceutical formulation according to claim 1; and optionally,
c) monitoring a neurotransmitter profile of the subject over time.

15. A method of reducing alcohol or drug cravings in a subject, comprising:

a) providing a subject suffering from alcohol or drug cravings;
b) administering to the subject an effective amount of the dietary supplement or pharmaceutical formulation according to claim 1; and optionally,
c) monitoring a neurotransmitter profile of the subject over time.

16. A method of reducing sugar cravings in a subject, comprising:

a) providing a subject suffering from sugar cravings;
b) administering to the subject an effective amount of the dietary supplement or pharmaceutical formulation according to claim 1; and optionally,
c) monitoring a neurotransmitter profile of the subject over time.

17. A method of treating a medical condition in a subject, comprising:

a) providing a subject suffering from a medical condition selected from one or more of the group consisting of depression, obsessive compulsive disorder, panic attacks, schizophrenia, seasonal affective disorder, PMS, attention deficit disorder (ADD), attention deficit hyperactivity disorder (ADHD), learning disabilities, autism, Post Traumatic Stress Disorder (PTSD), anxiety, chronic pain syndromes, fibromyalgia, irritable bowel syndrome, obesity, migraine headaches, and insomnia;
b) administering to the subject an effective amount of the pharmaceutical formulation according to claim 1; and optionally,
c) monitoring a neurotransmitter profile of the subject over time.

18. The dietary supplement or pharmaceutical according to claim 1, wherein the 5-hydroxy-tryptophan (5-HTP) is chemically synthesized or produced using recombinant DNA technology.

* * * * *